United States Patent
Sworen et al.

(10) Patent No.: US 10,011,617 B2
(45) Date of Patent: Jul. 3, 2018

(54) ISOCYANATE DERIVED ORGANOSILANES

(71) Applicant: THE CHEMOURS COMPANY FC LLC, Wilmington, DE (US)

(72) Inventors: John Christopher Sworen, Chadds Ford, PA (US); Gerald Oronde Brown, Wilmington, DE (US); Tatsiana Haidzinskaya, Newark, DE (US); Ewa Kohler, West Chester, PA (US)

(73) Assignee: THE CHEMOURS COMPANY FC, LLC, Wilmington, DE (US)

(*) Notice: Subject to any disclaimer, the term of this patent is extended or adjusted under 35 U.S.C. 154(b) by 0 days.

(21) Appl. No.: 14/847,199

(22) Filed: Sep. 8, 2015

(65) Prior Publication Data

US 2016/0090392 A1    Mar. 31, 2016

Related U.S. Application Data

(60) Provisional application No. 62/055,816, filed on Sep. 26, 2014.

(51) Int. Cl.

| | | |
|---|---|---|
| C07F 7/10 | (2006.01) | |
| C07F 7/28 | (2006.01) | |
| C09C 3/12 | (2006.01) | |
| C07F 7/18 | (2006.01) | |
| C09C 1/36 | (2006.01) | |
| C09C 1/40 | (2006.01) | |
| C09C 1/04 | (2006.01) | |
| C09C 1/30 | (2006.01) | |

(52) U.S. Cl.
CPC ............ C07F 7/10 (2013.01); C07F 7/1836 (2013.01); C07F 7/28 (2013.01); C09C 1/043 (2013.01); C09C 1/309 (2013.01); C09C 1/3072 (2013.01); C09C 1/3081 (2013.01); C09C 1/3669 (2013.01); C09C 1/3684 (2013.01); C09C 1/3692 (2013.01); C09C 1/407 (2013.01); C09C 3/12 (2013.01); C01P 2004/64 (2013.01)

(58) Field of Classification Search
CPC ................ C07F 7/10; C07F 7/28; C09C 3/12
See application file for complete search history.

(56) References Cited

U.S. PATENT DOCUMENTS

| | | |
|---|---|---|
| 4,297,290 A | 10/1981 | Stockburger |
| 5,256,706 A | 10/1993 | Carpenter et al. |
| 6,534,568 B1 | 3/2003 | Katz et al. |
| 8,729,257 B2 | 5/2014 | Dai et al. |
| 2005/0136264 A1 | 6/2005 | Dams et al. |
| 2006/0147645 A1 | 7/2006 | Dams et al. |
| 2006/0180549 A1 | 8/2006 | Liu et al. |
| 2011/0151218 A1 | 6/2011 | Meyer Zu Berstenhorst et al. |
| 2014/0004353 A1 | 1/2014 | Birkett et al. |

FOREIGN PATENT DOCUMENTS

| | | |
|---|---|---|
| CN | 102765774 | 11/2012 |
| CN | 102765844 | 11/2012 |
| CN | 102818790 | 12/2012 |
| CN | 103656622 | 3/2014 |
| EP | 0157218 A1 | 3/1985 |
| EP | 376883 | 7/1990 |
| EP | 0451709 | 10/1991 |
| EP | 0640611 A1 | 3/1995 |
| EP | 0507727 | 1/1997 |
| EP | 0864622 A2 | 9/1998 |
| EP | 0950662 A1 | 10/1999 |
| EP | 1035190 | 9/2000 |
| FR | 2954132 | 6/2011 |
| JP | 10330386 | 12/1998 |
| JP | 2002053805 | 2/2002 |
| JP | 2009242350 | 10/2009 |
| WO | 199632970 | 10/1996 |
| WO | 199638453 | 12/1996 |
| WO | 199801457 | 1/1998 |
| WO | 199935148 | 7/1999 |
| WO | 199940140 | 8/1999 |
| WO | 200112693 | 2/2001 |
| WO | 200193682 | 12/2001 |
| WO | 200240614 | 5/2002 |
| WO | 2003025539 | 3/2003 |
| WO | 2003091217 | 11/2003 |
| WO | 2004084634 | 10/2004 |
| WO | 2004099124 | 11/2004 |
| WO | 2006012957 | 2/2006 |
| WO | 2006137774 | 12/2006 |
| WO | 2008068198 | 6/2008 |
| WO | 2008112150 | 9/2008 |
| WO | 2008121360 | 10/2008 |
| WO | 2009009527 | 1/2009 |
| WO | 2009015164 | 1/2009 |
| WO | 2010069854 | 6/2010 |
| WO | 2010127805 | 11/2010 |
| WO | 2011006453 | 1/2011 |

(Continued)

OTHER PUBLICATIONS

Serebrennikova et al., caplus an 1971:449205.*
Furukawa-et-al., 1989, caplus an 1989:596048.*
Marat et al., 2016, caplus an 2016:1896658.*
Sagasaki et al., 2016, caplus an 2016:1878693.*
Nakamura et al., 2014, caplus an 2014:1344543.*
Ryu et al., 2014, caplus an 2014:966120.*
Yamasaki et al., 2008, caplus an 2008:419117.*
International Search Report, PCT—US2015/048808, dated Nov. 17, 2015.
Bommelaer, J. et al. J. Fluorine Chem. 1991, 55(1), 79-83.
Bovenkamp, J. W. et al. Ind. Eng. Chem. Prod. Res. Dev. 1981, 20(1), 130-133.

(Continued)

*Primary Examiner* — Sun Jae Yoo

(57) ABSTRACT

The invention relates to isocyanate derived organosilanes and the use thereof. The isocyanate derived organosilanes can be reacted with inorganic substrates, such as oxide particles, to result in a surface modified inorganic substrate.

16 Claims, No Drawings

(56) References Cited

FOREIGN PATENT DOCUMENTS

| | | |
|---|---|---|
| WO | 2011017538 | 2/2011 |
| WO | 2011017547 | 2/2011 |
| WO | 2012004199 | 1/2012 |
| WO | 2012040924 | 4/2012 |
| WO | 2012041227 | 4/2012 |
| WO | 2012166916 | 12/2012 |
| WO | 2014025385 | 2/2014 |

OTHER PUBLICATIONS

Howarter, J. et al. Polym. Preprints (American Chemical Society, Division of Polymer Chemistry) 2005, 46(2), 21-22.

Liang et al., Design and Synthesis of Lipidic Organoalkoxysilanes for the Self-Assembly of Liposomal Nanohybrid Cerasomes with Controlled Drug Release Properties, Chemistry—A European Journal (2013), 19(47).

Kricheldorf et al., Telechelic polylactones functionalized with trimethoxysilyl groups, Polymer (2005), 46(26), 12103-12108.

Bemiller, James, "Carbohydrates", Kirk-Othmer Encyclopedia of Chemical Technology, John Wiley & Sons, published online Jan. 16, 2004, vol. 4, pp. 696-733.

Arkles, Barry, "Silicon Compounds, Silicon Esters", Kirk-Othmer Encyclopedia of Chemical Technology, John Wiley & Sons, published online Dec. 4, 2000.

Streitwieser, A. et al., "Carbohydrates", Introduction to Organic Chemistry, Fourth Edition, MacMillan Publishing Company, 1992, pp. 903-943.

\* cited by examiner

ISOCYANATE DERIVED ORGANOSILANES

BACKGROUND OF THE INVENTION

Fluoroalkyl silanes are a class of compounds useful for various industrial purposes. For example, fluoroalkyl silanes which have hydrolysable groups (called hydrolysable fluoroalkyl silanes), are compounds useful as surface treatment agents which provide durable hydrophobic and oleophobic coatings. In general, hydrolysable fluoroalkyl silanes can be represented with the following formula: $(RO-)_3Si-R_T$ wherein R is H or an alkyl; and $R_T$ is a monovalent organic compound terminated by a perfluoroalkyl group. When used to coat a surface, the $(RO-)_3$ moiety reacts (via hydrolysis) with various chemical groups of the surface (e.g. hydroxyl, amine, or other reactive groups) thereby bonding the fluoroalkyl silane to the surface The $R_T$ moiety comprises a divalent organic linking group which links the silicon atom to a terminal group rich in fluorine atoms whose unique electronic properties impart desirable hydrophobic and oleophobic properties in a surface coating.

Efforts have been made to engineer fluoroalkyl silanes by incorporating $R_T$ moieties which have different divalent organic linking groups which link to the silicon atom of the fluoroalkyl silane. Examples of such divalent organic linking groups include esters, sulfonamides, amides, ethers, thioethers, arylenes, urethanes, and hydrines as discussed by EP 0157218 A1; JP 2002053805 A; EP 0950662 A1; EP 0640611 A1; US 2006147645 A1; US 2005136264 A1; EP 864622 A2 as well as Bommelaer, J. et al. *J. Fluorine Chem.* 1991, 55(1), 79-83; Bovenkamp, J. W. et al. *Ind. Eng. Chem. Prod. Res. Dev.* 1981, 20(1), 130-133; Howarter, J. et al. *Polym. Preprints* (American Chemical Society, Division of Polymer Chemistry) 2005, 46(2), 21-22).

There remains a need for additional silane materials that can be used as coating materials. The present invention provides such additional silane materials.

BRIEF SUMMARY OF THE INVENTION

The present invention relates to isocyanate derived organosilanes which can be formed by reacting an isocyanate represented by Formula (III):

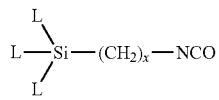

(III)

wherein:
L is independently chosen from hydrolysable or non-hydrolysable monovalent group, in an aspect of the invention L is independently chosen from H, $C_1$-$C_2$ alkyl, or OR, where R is H or $C_1$-$C_4$ alkyl. In a further aspect of the invention L is $CH_3$.

with at least one isocyanate-reactive compound selected from the group consisting of a cyclic or acyclic sugar alcohol which is substituted with at least one —$R^1$, —C(O)$R^1$, —$(CH_2CH_2O)_n(CH(CH_3)CH_2O)_mR^2$, —$(CH_2CH_2O)_n$(CH($CH_3$)$CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently —H, or a linear or branched alkyl group having 6 to 30 carbons optionally comprising at least 1 unsaturated bond, or mixtures thereof.

The isocyanate derived organosilanes which can be formed by the above reaction can be represented by Formula (I):

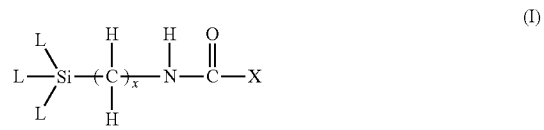

(I)

wherein:
x is independently an integer from 1 to 12;
L is independently chosen from hydrolysable or non-hydrolysable monovalent group, in an aspect of the invention L is independently chosen from H, $C_1$-$C_2$ alkyl, or OR, where R is H or $C_1$-$C_4$ alkyl, in a further aspect of the invention L is $CH_3$; and
X is at least one residue of a cyclic or acyclic sugar alcohol which is substituted with at least one —$R^1$, —C(O)$R^1$, —$(CH_2CH_2O)_n(CH(CH_3)CH_2O)_mR^2$, —$(CH_2CH_2O)_n$(CH($CH_3$)$CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently —H, or a linear or branched alkyl group having 6 to 30 carbons optionally comprising at least 1 unsaturated bond, or mixtures thereof.

The present invention also relates to surface modified inorganic substrates. As used herein, "inorganic substrates" include any suitable form, such as plates, fibers, particles, etc. In an aspect of the invention, inorganic substrates include oxides, and particularly oxide particles. For simplicity, oxide particles will be used hereinafter, but it should be understood that the invention relates broadly to inorganic substrates, defined above. The surface modified inorganic oxide particles can comprise an oxide of M wherein M is independently selected from the group consisting of Si, Ti, Zn, Zr, Mn, Al, and combinations thereof; said particles having an at least partial surface covalently bonded to at least one organosilane group represented by Formula (IV):

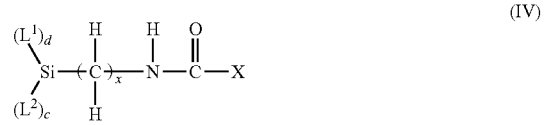

(IV)

wherein:
$L^1$ represents an oxygen covalently bonded to an M; X is at least one residue of a cyclic or acyclic sugar alcohol which is substituted with at least one —$R^1$, —C(O)$R^1$, —$(CH_2CH_2O)_n(CH(CH_3)CH_2O)_mR^2$, —$(CH_2CH_2O)_n$(CH($CH_3$)$CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently —H, or a linear or branched alkyl group having 6 to 30 carbons optionally comprising at least 1 unsaturated bond, or mixtures thereof. and each $L^2$ independently selected from the group consisting of H, a $C_1$-$C_2$ alkyl, and OH; d and c are integers such that: $d \geq 1$, $c \geq 0$, $d+c=3$.

DETAILED DESCRIPTION OF THE INVENTION

The present invention relates to isocyanate derived organosilanes which can be formed by reacting an isocyanate represented by Formula (III):

wherein:

L is independently chosen from hydrolysable or non-hydrolysable monovalent group, in an aspect of the invention L is independently chosen from H, $C_1$-$C_2$ alkyl, or OR, where R is H or $C_1$-$C_4$ alkyl, in a further aspect of the invention L is $CH_3$, with at least one isocyanate-reactive compound selected from the group consisting of a cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently —H, or a linear or branched alkyl group having 6 to 30 carbons optionally comprising at least 1 unsaturated bond, or mixtures thereof.

The at least one isocyanate-reactive compound comprises a cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof. The reaction of the substituted sugar alcohol with the isocyanate component will yield a urethane linkage with residues of the substituted sugar alcohol and of the isocyanate. The term "residue of a cyclic or acyclic sugar alcohol" is herein defined as the molecular structure of a cyclic or acyclic sugar alcohol when one or more H atoms has been removed from a hydroxyl group —OH. The urethane functional group may be formed by any suitable method, including by reacting an isocyanate with a cyclic or acyclic sugar alcohol which is substituted with at least one —$R^1$; —$C(O)R^1$; —$(CH_2CH_2O)_n(CH(CH_3)CH_2O)_mR^2$; —$(CH_2CH_2O)_n(CH(CH_3)CHO)_mC(O)R^1$; or mixtures thereof. The term "residue of an isocyanate" is herein defined as the molecular structure of an isocyanate where all isocyanate groups NCO have been removed.

The cyclic or acyclic sugar alcohol is selected from a saccharide, reduced sugar, aminosaccharide, aldonic acid, or aldonic acid lactone, and is substituted with at least one —$R^1$; —$C(O)R^1$; —$(CH_2CH_2O)_n(CH(CH_3)CH_2O)_mR^2$; —$(CH_2CH_2O)_n(CH(CH_3)CH_2O)_mC(O)R^1$; or mixtures thereof. The substituted sugar alcohols may be formed by reacting at least one sugar alcohol with at least one fatty acid or alkoxylated fatty acid. This step can be performed by any suitable esterification process. For example, U.S. Pat. No. 4,297,290 describes the synthesis of sorbitan esters, where an anhydro sorbitol is reacted with a fatty acid in the presence of an alkaline catalyst. Examples of such sugar alcohols include but are not limited to aldoses and ketoses such as those compounds derived from tetroses, pentoses, hexoses, and heptoses. Specific examples include glucose, glyceraldehyde, erythrose, arabinose, ribose, arabinose, allose, altrose, mannose, xylose, lyxose, gulose, galactose, talose, fructose, ribulose, mannoheptulose, sedoheptulose, threose, erythritol, threitol, glucopyranose, mannopyranose, talopyranose, allopyranose, altropyranose, idopyranose, gulopyranose, glucitol, mannitol, erythritol, sorbitol, arabitol, xylitol, ribitol, galactitol, fucitol, iditol, inositol, pentaerythritol, dipentaerythritol, volemitol, gluconic acid, glyceric acid, xylonic acid, galactaric acid, ascorbic acid, citric acid, gluconic acid lactone, glyceric acid lactone, xylonic acid lactone, glucosamine, galactosamine, or mixtures thereof. The cyclic or acyclic sugar alcohols used in this invention are substituted with at least one —$R^1$; —$C(O)R^1$; —$(CH_2CH_2O)_n(CH(CH_3)CH_2O)_mR^2$; or —$(CH_2CH_2O)_n(CH(CH_3)CH_2O)_mC(O)R^1$ by any suitable method, including esterification with a fatty acid, to form hydroxy-functional substituted sugar alcohols. Suitable fatty acids (b") include, but are not limited to, caprylic acid, capric acid, lauric acid, mysteric acid, palmitic acid, stearic acid, arachidic acid, behenic acid, lignoceric acid, palmitoleic acid, lineolic acid, oleic acid, erucic acid, and mixtures thereof. In one embodiment, $R^1$ is a linear or branched alkyl group having 7 to 29 carbons, in another embodiment, $R^1$ is a linear or branched alkyl group having 9 to 29 carbons, and in another embodiment, $R^1$ is a linear or branched alkyl group having 11 to 21 carbons. In one embodiment, $R^2$ is a linear or branched alkyl group having 8 to 30 carbons, in another embodiment, $R^2$ is a linear or branched alkyl group having 10 to 30 carbons, and in another embodiment, $R^2$ is a linear or branched alkyl group having 12 to 22 carbons.

In one embodiment, the isocyanate-reactive compound is selected from Formulas (IIa), (IIb), or (IIc):

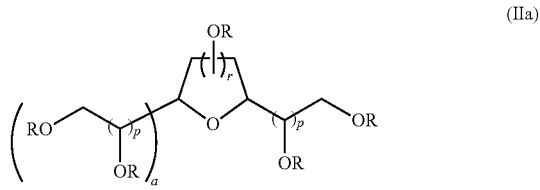

(IIa)

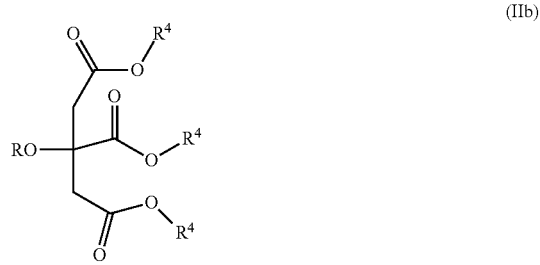

(IIb)

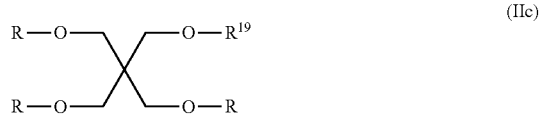

(IIc)

wherein each R is independently —H; —R$^1$; —C(O)R$^1$; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$; each n is independently 0 to 20; each m is independently 0 to 20; m+n is greater than 0; r is 1 to 3; a is 0 or 1; p is independently 0 to 2; provided that a is 0 when r is 3; each R$^1$ is independently a linear or branched alkyl group having 5 to 29 carbons optionally comprising at least 1 unsaturated bond; each R$^2$ is independently —H, or a linear or branched alkyl group having 6 to 30 carbons optionally comprising at least 1 unsaturated bond;
or mixtures thereof, provided when Formula (IIa) is chosen, then at least one R is —H and at least one R is a —R$^1$; —C(O)R$^1$; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$; each R$^4$ is independently —H, a linear or branched alkyl group having 6 to 30 carbons optionally comprising at least 1 unsaturated bond, or combinations thereof; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$; provided when Formula (IIb) is chosen, then at least one R or R$^4$ is —H; and at least one R or R$^4$ is a linear or branched alkyl group optionally comprising at least 1 unsaturated bond, or combinations thereof; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$; and each R$^{19}$ is —H, —C(O)R$^1$, or —CH$_2$C[CH$_2$OR]$_3$, provided when Formula (IIc) is chosen, then at least one R$^{19}$ or R is —H; and at least one R$^{19}$ or R is —C(O)R$^1$, —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$.

In Formulas (IIa), (IIb), or (IIc), the —(CH$_2$CH$_2$O)— represents oxyethylene groups (EO) and —(CH(CH$_3$)CH$_2$O)— represents oxypropylene groups (PO). These compounds can contain only EO groups, only PO groups, or mixtures thereof. These compounds can also be present as a tri-block copolymer designated PEG-PPG-PEG (polyethylene glycol-polypropylene glycol-polyethylene glycol), for example.

Where the isocyanate-reactive compound is from Formula (IIa), any suitable substituted reduced sugar alcohol may be employed, including esters of 1,4-sorbitan, esters of 2,5-sorbitan, and esters of 3,6-sorbitan. In one embodiment, the isocyanate-reactive compound is selected from Formula (IIa) to be Formula (IIaa):

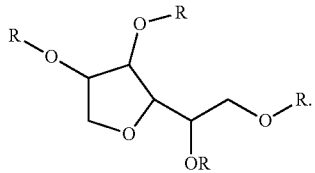

(IIaa)

In one embodiment, at least one R is H, and at least one R is —C(O)R$^1$ or R$^1$. Compounds used to form residues of Formula (IIaa), having at least one R as —H and at least one R selected from —C(O)R$^1$, are commonly known as alkyl sorbitans. These sorbitans can be mono-substituted, di-substituted, or tri-substituted with —C(O)R$^1$. It is known that commercially available sorbitans, such as SPAN, contain a mixture of the various sorbitans ranging from where each R is H (un-substituted), and sorbitans where each R is —C(O)R$^1$ (fully substituted); wherein R$^1$ is a linear or branched alkyl group having 5 to 29 carbons; and mixtures of various substitutions thereof. The commercially available sorbitans may also include amounts of sorbitol, isosorbide, or other intermediates or byproducts.

In one embodiment, at least one R is —C(O)R$^1$, and R$^1$ is a linear or branched alkyl group having 5 to 29 carbons. In another embodiment, R$^1$ is a linear or branched alkyl group having 7 to 21 carbons, and in a third embodiment, R$^1$ is a linear or branched alkyl group having 11 to 21 carbons. Preferred compounds used to form these residues include mono-, di-, and tri-substituted sorbitans derived from caprylic acid, capric acid, lauric acid, mysteric acid, palmitic acid, stearic acid, arachidic acid, behenic acid, lignoceric acid, and mixtures thereof. Particularly preferred compounds include mono-, di-, and tri-substituted sorbitan stearates or sorbitan behenins.

Optionally, R$^1$ is a linear or branched alkyl group having 5 to 29 carbons comprising at least 1 unsaturated bond. Examples of compounds used to form compounds of Formula (IIaa) wherein at least one R is selected from —C(O)R$^1$; and R$^1$ contains least 1 unsaturated bond, include, but are not limited to, sorbitan trioleate (i.e., wherein R$^1$ is —C$_7$H$_{14}$CH=CHC$_8$H$_{17}$). Other examples include but are not limited to mono-, di-, and tri-substituted sorbitans derived from palmitoleic acid, lineolic acid, arachidonic acid, and erucic acid.

In one embodiment, Formula (IIaa) is employed, wherein R is further limited to independently a —H; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$. In this embodiment, at least one R is independently —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$. In one aspect, R$^2$ is H and m is a positive integer such that the substitution is hydrophobic. Compounds of Formula (IIaa), wherein at least one R is —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$, wherein each m is independently 0 to 20, each n is independently 0 to 20, and n+m is greater than 0 are known as polysorbates and are commercially available under the tradename TWEEN. These polysorbates can be mono-substituted, di-substituted, or tri-substituted with alkyl groups R$^1$ or R$^2$. It is known that commercially available polysorbates, contain a mixture of the various polysorbates ranging from where each R$^2$ is H (unsubstituted), and polysorbates where each R$^1$ is a linear or branched alkyl group having 5 to 29 carbons (fully substituted); and mixtures of various substitutions thereof. Examples of compounds of Formula (IIa') include polysorbates such as polysorbate tristearate, and polysorbate monostearate. Examples of compounds of Formula (IIa') wherein m+n is greater than 0, and wherein R$^1$ comprises at least 1 unsaturated bond, include but are not limited to, polysorbate trioleate (wherein R$^1$ is C$_7$H$_{14}$CH=CHC$_8$H$_{17}$), are sold commercially under the name Polysorbate 80. Reagents may include mixtures of compounds having various values for R, R$^1$, and R$^2$, and may also include mixtures of compounds where R$^1$ comprises at least one unsaturated bond with compounds where R$^1$ is fully saturated.

In one embodiment, the isocyanate-reactive compound is selected from Formula (IIb). Compounds of Formula (IIb) are known as alkyl citrates. These citrates can be present as a mono-substituted, di-substituted, or tri-substituted compound with alkyl groups. It is known that commercially available citrates contain a mixture of the various citrates as well as citric acids from where R and each R$^4$ is —H, ranging to citrates where each R$^4$ is a linear or branched alkyl group having 6 to 30 carbons optionally comprising at least 1 unsaturated bond; and mixtures of various substitutions thereof. Mixtures of citrates having various values for R$^1$, R$^2$, and R$^4$ may be used, and may also include mixtures of compounds where $R^1$ comprises at least one unsaturated bond with compounds where $R^1$ is fully saturated. Alkyl citrates are also commercially available wherein m+n is greater than 0, $R^4$ is —$(CH_2CH_2O)_n(CH(CH_3)CH_2O)_mR^2$; or —$(CH_2CH_2O)_n(CH(CH_3)CH_2O)_mC(O)R^1$ and are present in the various substitutions from wherein R and each $R^2$ is H to wherein each $R^1$ and/or $R^2$ is a linear or branched alkyl group having 5 to 30 carbons optionally comprising at least 1 unsaturated bond. Examples of compounds of Formula (IIb) include, but are not limited to, trialkyl citrates.

In one embodiment, the isocyanate-reactive compound is selected from Formula (IIc). Compounds of Formula (IIc) are known as pentaerythriol esters. These pentaerythriol esters can be present as a mono-substituted, di-substituted, or tri-substituted with alkyl groups. It is known that commercially available pentaerythriol esters contain a mixture of the various pentaerythriol esters where $R^{19}$ and each R is —H, ranging to pentaerythriol esters where each R is —$C(O)R^1$, and $R^1$ is a linear or branched alkyl group having 5 to 29 carbons optionally comprising at least 1 unsaturated bond; and mixtures of various substitutions thereof. The pentaerythriol esters also may contain compounds with mixtures of different chain lengths for R, or mixtures of compounds where $R^1$ comprises at least one unsaturated bond with compounds where $R^1$ is fully saturated.

Compounds of Formulas (IIa), (IIb), and (IIc) can all be bio-based derived. By "bio-based derived", it is meant that at least 10% of the material can be produced from non-crude oil sources, such as plants, other vegetation, and tallow. In one embodiment, the substituted sugar alcohol is from about 10% to 100% bio-based derived. In one embodiment, the substituted sugar alcohol is from about 35% to 100% bio-based derived. In another embodiment, the substituted sugar alcohol is from about 50% to 100% bio-based derived. In one embodiment, the substituted sugar alcohol is from about 75% to 100% bio-based derived. In one embodiment, the substituted sugar alcohol is 100% bio-based derived. The average OH value of the substituted sugar alcohol compounds can range from just greater than 0 to about 230. In one embodiment, the average OH value is from about 10 to about 175, and in another embodiment, the average OH value is from about 25 to about 140.

The isocyanate derived organosilanes can be represented by Formula (I):

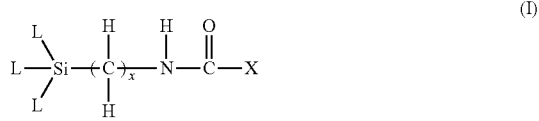

wherein:

x is an integer from 1 to 12;

L is independently chosen from hydrolysable or non-hydrolysable monovalent group, in an aspect of the invention L is independently chosen from H, $C_1$-$C_2$ alkyl, or OR, where R is H or $C_1$-$C_4$ alkyl, in a further aspect of the invention L is $CH_3$; and X is at least one residue of a cyclic or acyclic sugar alcohol which is substituted with at least one —$R^1$, —$C(O)R^1$, —$(CH_2CH_2O)_n(CH(CH_3)CH_2O)_mR^2$, —$(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; and each $R^2$ is independently —H, or a linear or branched alkyl group having 6 to 30 carbons optionally comprising at least 1 unsaturated bond, or mixtures thereof.

In one embodiment, the at least one residue of a cyclic or acyclic sugar alcohol is selected from Formulas (IIa'), (IIb'), or (IIc'):

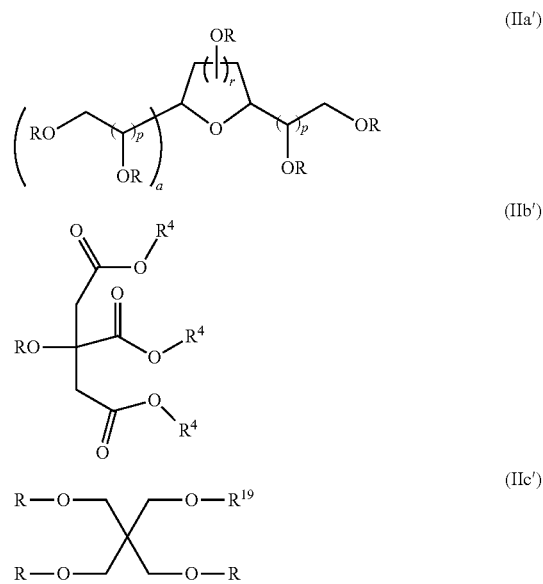

wherein each R is independently a direct bond to C=O of Formula (I); —H; —$R^1$; —$C(O)R^1$; —$(CH_2CH_2O)_n(CH(CH_3)CH_2O)_mR^2$; or —$(CH_2CH_2O)_n(CH(CH_3)CH_2O)_mC(O)R^1$; each n is independently 0 to 20; each m is independently 0 to 20; m+n is greater than 0; r is 1 to 3; a is 0 or 1; p is independently 0 to 2; provided that a is 0 when r is 3; each $R^1$ is independently a linear or branched alkyl group having 5 to 29 carbons optionally comprising at least 1 unsaturated bond; each $R^2$ is independently —H, or a linear or branched alkyl group having 6 to 30 carbons optionally comprising at least 1 unsaturated bond;

or mixtures thereof, provided when Formula (IIa) is chosen, then at least one R is a —$R^1$; —$C(O)R^1$; —$(CH_2CH_2O)_n(CH(CH_3)CH_2O)_mR^2$; or —$(CH_2CH_2O)_n(CH(CH_3)CH_2O)_mC(O)R^1$; each $R^4$ is independently a direct bond to C=O of Formula (I); —H, a linear or branched alkyl group having 6 to 30 carbons optionally comprising at least 1 unsaturated bond, or combinations thereof; —$(CH_2CH_2O)_n(CH(CH_3)CH_2O)_mR^2$; or —$(CH_2CH_2O)_n(CH(CH_3)CH_2O)_mC(O)R^1$; provided when Formula (IIb') is chosen, then at least one R or $R^4$ is a direct bond to C=O of Formula (I), or —H; and at least one R or $R^4$ is a linear or branched alkyl group optionally comprising at least 1 unsaturated bond, or combinations thereof; —$(CH_2CH_2O)_n(CH(CH_3)CH_2O)_mR^2$; or —$(CH_2CH_2O)_n(CH(CH_3)CH_2O)_mC(O)R^1$; and each $R^{19}$ is a direct bond to C=O of Formula (I); —H, —$C(O)R^1$, or —$CH_2C[CH_2OR]_3$, provided when Formula (IIc) is chosen, then at least one $R^{19}$ or R is a direct bond to C=O of Formula (I), or —H; and at least one $R^{19}$ or R is —$C(O)R^1$, —$(CH_2CH_2O)_n(CH(CH_3)CH_2O)_mR^2$; or —$(CH_2CH_2O)_n(CH(CH_3)CH_2O)_mC(O)R^1$.

In Formulas (IIa'), (IIb'), or (IIc'), the —(CH$_2$CH$_2$O)— represents oxyethylene groups (EO) and —(CH(CH$_3$)CH$_2$O)— represents oxypropylene groups (PO). These compounds can contain only EO groups, only PO groups, or mixtures thereof. These compounds can also be present as a tri-block copolymer designated PEG-PPG-PEG (polyethylene glycol-polypropylene glycol-polyethylene glycol), for example.

Where the at least one residue of a cyclic or acyclic sugar alcohol is from Formula (IIa'), any suitable substituted reduced sugar alcohol may be employed, including esters of 1,4-sorbitan, esters of 2,5-sorbitan, and esters of 3,6-sorbitan. In one embodiment, the at least one residue of a cyclic or acyclic sugar alcohol is selected from Formula (IIa') to be Formula (IIaa'):

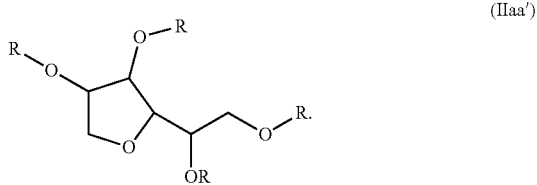

(IIaa')

In one embodiment, at least one R is a direct bond to C=O of Formula (I), or H, and at least one R is —C(O)R$^1$ or R$^1$. Compounds used to form residues of Formula (IIaa'), having at least one R as —H and at least one R selected from —C(O)R$^1$, are commonly known as alkyl sorbitans. These sorbitans can be mono-substituted, di-substituted, or tri-substituted with —C(O)R$^1$. It is known that commercially available sorbitans, such as SPAN, contain a mixture of the various sorbitans ranging from where each R is H (unsubstituted), and sorbitans where each R is —C(O)R$^1$ (fully substituted); wherein R$^1$ is a linear or branched alkyl group having 5 to 29 carbons; and mixtures of various substitutions thereof. The commercially available sorbitans may also include amounts of sorbitol, isosorbide, or other intermediates or byproducts.

In one embodiment, at least one R is —C(O)R$^1$, and R$^1$ is a linear or branched alkyl group having 5 to 29 carbons. In another embodiment, R$^1$ is a linear or branched alkyl group having 7 to 21 carbons, and in a third embodiment, R$^1$ is a linear or branched alkyl group having 11 to 21 carbons. Preferred compounds used to form these residues include mono-, di-, and tri-substituted sorbitans derived from caprylic acid, capric acid, lauric acid, mysteric acid, palmitic acid, stearic acid, arachidic acid, behenic acid, lignoceric acid, and mixtures thereof. Particularly preferred compounds include mono-, di-, and tri-substituted sorbitan stearates or sorbitan behenins.

Optionally, R$^1$ is a linear or branched alkyl group having 5 to 29 carbons comprising at least 1 unsaturated bond. Examples of compounds used to form compounds of Formula (IIaa) wherein at least one R is selected from —C(O)R$^1$; and R$^1$ contains least 1 unsaturated bond, include, but are not limited to, sorbitan trioleate (i.e., wherein R$^1$ is —C$_7$H$_{14}$CH=CHC$_8$H$_{17}$). Other examples include but are not limited to mono-, di-, and tri-substituted sorbitans derived from palmitoleic acid, lineolic acid, arachidonic acid, and erucic acid.

In one embodiment, Formula (IIaa') is employed, wherein R is further limited to independently a direct bond to C=O of Formula (I), —H; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$. In this embodiment, at least one R is independently —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$. In one aspect, R$^2$ is H and m is a positive integer such that the substitution is hydrophobic. Compounds of Formula (IIaa'), wherein at least one R is —(CH$_2$CH$_2$O)$_n$(CH(CH$_3$)CH$_2$O)$_m$R$^2$ or —(CH$_2$CH$_2$O)$_n$(CH(CH$_3$)CH$_2$O)$_m$C(O)R$^1$, wherein each m is independently 0 to 20, each n is independently 0 to 20, and n+m is greater than 0 are known as polysorbates and are commercially available under the tradename TWEEN. These polysorbates can be mono-substituted, di-substituted, or tri-substituted with alkyl groups R$^1$ or R$^2$. It is known that commercially available polysorbates, contain a mixture of the various polysorbates ranging from where each R$^2$ is H (unsubstituted), and polysorbates where each R$^1$ is a linear or branched alkyl group having 5 to 29 carbons (fully substituted); and mixtures of various substitutions thereof. Examples of compounds of Formula (IIa') include polysorbates such as polysorbate tristearate, and polysorbate monostearate. Examples of compounds of Formula (IIa') wherein m+n is greater than 0, and wherein R$^1$ comprises at least 1 unsaturated bond, include but are not limited to, polysorbate trioleate (wherein R$^1$ is C$_7$H$_{14}$CH=CHC$_8$H$_{17}$), are sold commercially under the name Polysorbate 80. Reagents may include mixtures of compounds having various values for R, R$^1$, and R$^2$, and may also include mixtures of compounds where R$^1$ comprises at least one unsaturated bond with compounds where R$^1$ is fully saturated.

In one embodiment, the at least one residue of a cyclic or acyclic sugar alcohol is selected from Formula (IIb'). Compounds used to form Formula (IIb') are known as alkyl citrates. These citrates can be present as a mono-substituted, di-substituted, or tri-substituted compound with alkyl groups. It is known that commercially available citrates contain a mixture of the various citrates as well as citric acids from where R and each R$^4$ is —H, ranging to citrates where each R$^4$ is a linear or branched alkyl group having 6 to 30 carbons optionally comprising at least 1 unsaturated bond; and mixtures of various substitutions thereof. Mixtures of citrates having various values for R$^1$, R$^2$, and R$^4$ may be used, and may also include mixtures of compounds where R$^1$ comprises at least one unsaturated bond with compounds where R$^1$ is fully saturated. Alkyl citrates are also commercially available wherein m+n is greater than 0, R$^4$ is —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$ and are present in the various substitutions from wherein R and each R$^2$ is H to wherein each R$^1$ and/or R$^2$ is a linear or branched alkyl group having 5 to 30 carbons optionally comprising at least 1 unsaturated bond. Examples of compounds of Formula (IIb') include, but are not limited to, trialkyl citrates.

In one embodiment, the at least one residue of a cyclic or acyclic sugar alcohol is selected from Formula (IIc'). Compounds used to form Formula (IIc') are known as pentaerythriol esters. These pentaerythriol esters can be present as a mono-substituted, di-substituted, or tri-substituted with alkyl groups. It is known that commercially available pentaerythriol esters contain a mixture of the various pentaerythriol esters where R$^{19}$ and each R is —H, ranging to pentaerythriol esters where each R is —C(O)R$^1$, and R$^1$ is a linear or branched alkyl group having 5 to 29 carbons optionally comprising at least 1 unsaturated bond; and mixtures of various substitutions thereof. The pentaerythriol esters also may contain compounds with mixtures of different chain lengths for R, or mixtures of compounds where R$^1$ comprises at least one unsaturated bond with compounds where R$^1$ is fully saturated.

The isocyanate derived organosilane can be made by reacting the isocyanate of Formula (III) with the at least one isocyanate-reactive compound described above.

The reaction product can be made in one step, including those compounds made with mixtures of the at least one isocyanate-reactive compound. In one embodiment, if more than one isocyanate-reactive compound is present, then the synthesis can be completed sequentially. A sequential addition is especially useful when employing substituted sugar alcohols with high OH numbers.

This reaction is typically conducted by charging a reaction vessel with the isocyanate and the at least one isocyanate-reactive compound. The order of reagent addition is not critical.

The specific weight of the reactants charged is based on their equivalent weights and on the working capacity of the reaction vessel, and is adjusted so that the isocyanate-reactive compound will be consumed in the first step. A suitable dry organic solvent free of isocyanate-reactive groups is typically used as a solvent. Ketones are the preferred solvents, and methylisobutylketone (MIBK) is particularly preferred for convenience and availability. The charge is agitated, and temperature adjusted to about 40° C. to 70° C. Typically, a catalyst such as iron(III) chloride in an organic solvent is then added, typically in an amount of from about 0.01 to about 1.0 weight % based on the dry weight of the composition, and the temperature is raised to about 80° C. to 100° C. A co-catalyst, such as sodium carbonate, may also be used. If water is to be added, the initial reaction is conducted so that less than 100% of the isocyanate groups are reacted. In the second step after holding for several hours, additional solvent, water, and optionally a second compound are added. In one embodiment the mixture is allowed to react for several more hours or until all of the isocyanate has been reacted. Additional water can then be added along with surfactants, if desired, to the urethane compounds and stirred until thoroughly mixed. Following a homogenization or sonification step, the organic solvent can be removed by evaporation at reduced pressure, and the remaining aqueous solution or dispersion of the compound of the present invention can be used as is or subjected to further processing. The aqueous composition comprises at least one compound of the present invention, a water carrier, and optionally one or more surfactants.

It will be apparent to one skilled in the art that many changes to any or all of the above procedures can also be used to optimize the reaction conditions for obtaining maximum yield, productivity, or product quality.

In a further embodiment, the isocyanate derived organosilane can be blended with at least one fluorosilane. The fluorosilane can be derived from an isocyanate and at least one fluorinated alcohol. The isocyanate comprises an isocyanate represented by Formula (III), which can be reacted with a suitable fluorinated alcohol. Any suitable fluorinated alcohol may be used. The fluorinated alcohol is represented by Formula (V):

where $R_f$ is a $C_1$ to $C_{20}$ perfluoroalkyl group optionally interrupted by $CH_2$, $CH_2CH_2$, $SO_2N$, $CFH$, $S$, or $O$; and $A$ is a direct bond or a $C_1$ to $C_6$ alkylene group. $R_f$ and $A$ may be linear or branched. In one aspect, the fluorinated alcohol is a telomer-based alcohol, where $R_f$ is a linear perfluoroalkyl group and A is $CH_2CH_2$. In one aspect, $R_f$ is a $C_2$ to $C_6$ linear or branched perfluoroalkyl group. Specific examples of fluorinated alcohols include but are not limited to $R_fOH$, $R_fCH_2CH_2OH$, $R_fSO_2NHCH_2CH_2OH$, $R_fCH_2CH_2SCH_2CH_2OH$, $R_fCH_2CH_2CF_2CF_2CH_2CH_2OH$, $R_fCH_2CH_2(CF_2CF_2CH_2CH_2)_2OH$, $R_fCH_2CF_2CH_2CH_2OH$, $R_fCH_2CF_2CH_2CF_2CH_2CH_2OH$, $R_fOCF_2CF_2CH_2CH_2OH$, $R_fCH_2OCH_2CH_2OH$, $R_fCHFCH_2CH_2OH$, $R_fCH_2O(CH_2)_6OH$, $(CF_3)_2CFCH_2CH_2OH$, $(CF_3)_2CFCH_2CH_2CH_2OH$, $R_fCH_2CH_2SO_2NHCH_2CH_2OH$, $R_fCH_2CH_2SO_2N(CH_3)CH_2CH_2OH$, $R_fCH_2CH_2SO_2N(CH_2CH_3)CH_2CH_2OH$, $R\!-\!(CF(CF_3)CF_2O)_yCH_2OH$, $CF_2\!=\!CFOCF_2CF(CF_3)OCF_2CF_2CH_2OH$, or $R_fCH_2OC_2F_4CH_2OCH_2CH_2OH$.

Any suitable ratio of isocyanate derived organosilanes and silane derived from an isocyanate and at least one fluorinated alcohol can be used.

The present invention also relates to surface modified inorganic oxide particles. The surface modified inorganic oxide particles can comprise an oxide of M wherein M is independently selected from the group consisting of Si, Ti, Zn, Zr, Mn, Al, and combinations thereof; said particles having an at least partial surface covalently bonded to at least one organosilane group represented by Formula (IV):

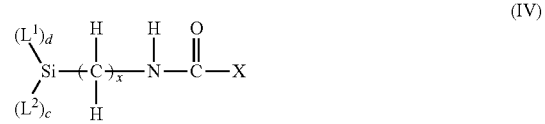

wherein:

x is an integer from 1 to 12;

$L^1$ represents an oxygen covalently bonded to an M; X is at least one residue of a cyclic or acyclic sugar alcohol which is substituted with at least one $-R^1$, $-C(O)R^1$, $-(CH_2CH_2O)_n(CH(CH_3)CH_2O)_mR^2$, $-(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently $-H$, or a linear or branched alkyl group having 6 to 30 carbons optionally comprising at least 1 unsaturated bond, or mixtures thereof; and each $L^2$ independently selected from the group consisting of H, a $C_1$-$C_2$ alkyl, and OH; d and c are integers such that: d≥1, c≥0, d+c=3.

The hydrophobized inorganic particles of the present invention can be made by dispersing inorganic particles in a non-polar solvent (e.g. toluene) and adding to this dispersion the desired organosilane. The dispersion is then heated to an elevated temperature (e.g. 80-100° C.) for about 8-10 hours. The dispersion is then allowed to cool to ambient temperature (about 20° C.). The dispersion is then placed in a centrifuge, the solvent is decanted, and the resulting inorganic particles are washed with fresh solvent. Washing is preferably done at least twice. The washed inorganic particles are then dried in an oven at elevated temperature (about 100-110° C.). The resulting dried inorganic particles can be re-dispersed in a non-polar solvent (e.g. toluene) and additional organosilane can be added to this dispersion by repeating the entire procedure described in this paragraph.

The procedure for making hydrophobized inorganic particles in the preceding paragraph is preferable and is known as the "convergent" approach. Alternatively, some of the hydrophobized inorganic particles of the present invention can also be made via a "divergent" approach wherein "functionalized inorganic particles" are made by reacting untreated inorganic particles with a first precursor wherein the first precursor comprises a silicon atom bonded to at least one terminal hydrolysable group which reacts with the surface of the inorganic particle thereby creating a covalent bond between the first precursor and the inorganic particle. The first precursor further comprises a terminal reactive group (e.g. an amine or an isocyante derived from an amine or an isothiocyanate derived an amine) thereby creating functionalized inorganic particles having "anchors" which comprise the terminal reactive group. These functionalized inorganic particles are then reacted with a second precursor wherein the second precursor comprises a corresponding reactive group (e.g. a terminal amine, an isocyanate, an isothiocyanate, vinyl, sulfonyl chloride, or sulfonamide) capable of reacting with the terminal reactive group of the "anchors." The second precursor is also known herein by the term "capping agent." An example of a useful first precursor and second precursor combination is wherein the first precursor comprises a terminal amine group and the second precursor comprises a terminal isocyanate, isothiocyanate, vinyl, sulfonyl chloride, or sulfonamide.

Inorganic particles useful to the invention include any inorganic particles that have reactive groups on the surface thereof wherein such groups are capable of reacting with the hydrolysable groups of the organosilanes (or precursors thereof) of the invention thereby creating a covalent bond between the inorganic particle and the organosilane (or precursor thereof). Particularly useful inorganic particles are oxides, such as oxides of silicon, titanium, zinc, zirconium, manganese, and aluminum.

The surface modified inorganic oxide particles can be provided with an at least partial surface coating (or a complete surface coating or shell) comprising a second polymer. In one embodiment, the second polymer is a copolymer that comprises at least one additional repeat unit from an ethylenically unsaturated monomer having a functional group selected from a linear or branched hydrocarbon, linear or branched fluorocarbon, ether, alcohol, anhydride, oxyalkylene, ester, formate, carboxylic acid, carbamate, urea, amine, amide, sulfonate, sulfonic acid, sulfonamide, halide, saturated or unsaturated cyclic hydrocarbon, morpholine, pyrrolidine, piperidine, or mixtures thereof. The ethylenically unsaturated monomer can be any monomer having an ethylenically unsaturated bond with a functional group described above, including but not limited to linear or branched alkyl(meth)acrylates, amino and diamino(meth)acrylates, linear or branched fluoroalkyl(meth)acrylates optionally interrupted by O, $CH_2$, $CH_2CH_2$, or $SO_2NH$, alkoxylated (meth)acrylates, (meth)acylic acid, vinyl or vinylidene chloride, glycidyl(meth)acrylate, vinyl acetate, hydroxyalkylene(meth)acrylate, urethane or urea(meth)acrylates, (meth)acrylamides including N-methyloyl(meth)acrylamide, alkoxyalkyl(meth)acrylamide, styrene, alpha-methylstyrene, chloromethyl-substituted styrene, ethylenediol di(meth)acrylate, 2-acrylamido-2-methyl-1-propane sulfonic acid (AMPS), and maleic anhydride.

Specific fluorinated ethylenically unsaturated monomers used to incorporate fluoroalkyl functionality into the first or second poly(meth)acrylate polymer include but are not limited to $R_fCH_2CH_2OC(O)CR^3\!=\!CH_2$, $R_fSO_2NHCH_2CH_2OC(O)CR^3\!=\!CH_2$, $R_fCH_2CH_2SCH_2CH_2OC(O)CR^3\!=\!CH_2$, $R_fCH_2CH_2CF_2CF_2CH_2CH_2OC(O)CR^3\!=\!CH_2$, $R_fCH_2CH_2(CF_2CF_2CH_2)_2OC(O)CR^3\!=\!CH_2$, $R_fCH_2CF_2CH_2CH_2OC(O)CR^3\!=\!CH_2$, $R_fCH_2CF_2CH_2CF_2CH_2CH_2OC(O)CR^3\!=\!CH_2$, $R_fOCF_2CF_2CH_2CH_2OC(O)CR^3\!=\!CH_2$, $R_fCH_2OCH_2CH_2OC(O)CR^3\!=\!CH_2$, $R_fCHFCH_2CH_2OH$, $R_fCH_2O(CH_2)_6OC(O)CR^3\!=\!CH_2$, $(CF_3)_2CFCH_2CH_2OC(O)CR^3\!=\!CH_2$, $(CF_3)_2CFCH_2CH_2CH_2OC(O)CR^3\!=\!CH_2$, $R_fCH_2CH_2SO_2NHCH_2CH_2OC(O)CR^3\!=\!CH_2$, $R_fCH_2CH_2SO_2N(CH_3)CH_2CH_2OC(O)CR^3\!=\!CH_2$, $R_fCH_2CH_2SO_2N(CH_2CH_3)CH_2CH_2OC(O)CR^3\!=\!CH_2$, $R\!-\!(CF(CF_3)CF_2O)_yCH_2OC(O)CR^3\!=\!CH_2$, $CF_2\!=\!CFOCF_2CF(CF_3)OCF_2CF_2CH_2OC(O)CR^3\!=\!CH_2$, or $R_fCH_2OC_2F_4CH_2OCH_2CH_2OC(O)CR^3\!=\!CH_2$, where $R_f$ is a linear or branched fluoroalkyl of $C_1$-$C_{20}$, or $CH_2\!=\!CH\!-\!COO\!-\!C_2H_4\!-\!N(CH_3)\!-\!SO_2\!-\!C_2H_4\!-\!C_6F_{13}$, 2-[methyl[(3,3,4,4,5,5,6,6,6-nonfluorohexyl)sulfonyl]amino]ethyl acrylate, 2-[methyl[(3,3,4,4,5,5,6,6,7,7,8,8,8-tridecafluorooctyl)sulfonyl]amino]ethyl methacrylate, or 2-[[(3,3,4,4,5,5,6,6,7,7,8,8,8-tridecafluorooctyl)sulfonyl]amino]ethyl methacrylate. In one embodiment, $R_f$ is a $C_2$ to $C_6$ perfluoroalkyl.

As stated earlier, the "convergent" approach is preferable for making the hydrophobized inorganic particles of the invention. Organosilanes useful in the convergent approach are represented by Formula (I):

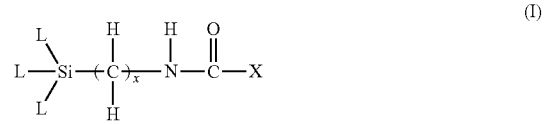

wherein:

x is an integer from 1 to 12;

L is independently chosen from hydrolysable or non-hydrolysable monovalent group, in an aspect of the invention L is independently chosen from H, $C_1$-$C_2$ alkyl, or OR, where R is H or $C_1$-$C_4$ alkyl, in a further aspect of the invention L is $CH_3$;

X is at least one residue of a cyclic or acyclic sugar alcohol which is substituted with at least one $-R^1$, $-C(O)R^1$, $-(CH_2CH_2O)_n(CH(CH_3)CH_2O)_mR^2$, $-(CH_2CH_2O)_n(CH(CH_3)CH_2O)_mC(O)R^1$, or mixtures thereof; where the cyclic or acyclic sugar alcohol is selected from a saccharide, reduced sugar, aminosaccharide, aldonic acid, or aldonic acid lactone; wherein each n is independently 0 to 20; each m is independently 0 to 20; m+n is greater than 0; each $R^1$ is independently a linear or branched alkyl group having 5 to 29 carbons optionally comprising at least 1 unsaturated bond; each $R^2$ is independently $-H$, or a linear or branched alkyl group having 6 to 30 carbons optionally comprising at least 1 unsaturated bond, or mixtures thereof; and In one embodiment, the at least one residue of a cyclic or acyclic sugar alcohol is selected from Formulas (IIa'), (IIb'), or (IIc'):

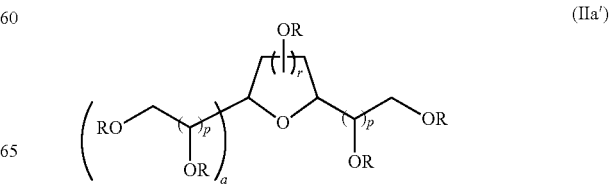

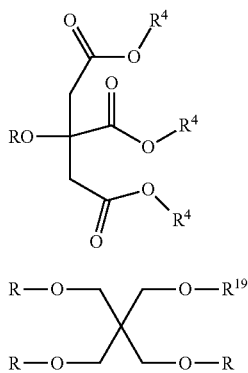

(IIb')

(IIc')

(IIaa')

wherein each R is independently a direct bond to C═O of Formula (I); —H; —R¹; —C(O)R¹; —(CH₂CH₂O)ₙ(CH(CH₃)CH₂O)ₘR²; or —(CH₂CH₂O)ₙ(CH(CH₃)CH₂O)ₘC(O)R¹; each n is independently 0 to 20;

each m is independently 0 to 20; m+n is greater than 0; r is 1 to 3; a is 0 or 1; p is independently 0 to 2; provided that a is 0 when r is 3; each R¹ is independently a linear or branched alkyl group having 5 to 29 carbons optionally comprising at least 1 unsaturated bond; each R² is independently —H, or a linear or branched alkyl group having 6 to 30 carbons optionally comprising at least 1 unsaturated bond;

or mixtures thereof, provided when Formula (IIa) is chosen, then at least one R is a —R¹; —C(O)R¹; —(CH₂CH₂O)ₙ(CH(CH₃)CH₂O)ₘR²; or —(CH₂CH₂O)ₙ(CH(CH₃)CH₂O)ₘC(O)R¹; each R⁴ is independently a direct bond to C═O of Formula (I); —H, a linear or branched alkyl group having 6 to 30 carbons optionally comprising at least 1 unsaturated bond, or combinations thereof; —(CH₂CH₂O)ₙ(CH(CH₃)CH₂O)ₘR²; or —(CH₂CH₂O)ₙ(CH(CH₃)CH₂O)ₘC(O)R¹; provided when Formula (IIb') is chosen, then at least one R or R⁴ is a direct bond to C═O of Formula (I), or —H; and at least one R or R⁴ is a linear or branched alkyl group optionally comprising at least 1 unsaturated bond, or combinations thereof; —(CH₂CH₂O)ₙ(CH(CH₃)CH₂O)ₘR²; or —(CH₂CH₂O)ₙ(CH(CH₃)CH₂O)ₘC(O)R¹; and each R¹⁹ is a direct bond to C═O of Formula (I); —H, —C(O)R¹, or —CH₂C[CH₂OR]₃, provided when Formula (IIc) is chosen, then at least one R¹⁹ or R is a direct bond to C═O of Formula (I), —H; and at least one R¹⁹ or R is —C(O)R¹, —(CH₂CH₂O)ₙ(CH(CH₃)CH₂O)ₘR²; or —(CH₂CH₂O)ₙ(CH(CH₃)CH₂O)ₘC(O)R¹.

In Formulas (IIa'), (IIb'), or (IIc'), the —(CH₂CH₂O)— represents oxyethylene groups (EO) and —(CH(CH₃)CH₂O)— represents oxypropylene groups (PO). These compounds can contain only EO groups, only PO groups, or mixtures thereof. These compounds can also be present as a tri-block copolymer designated PEG-PPG-PEG (polyethylene glycol-polypropylene glycol-polyethylene glycol), for example.

Where the at least one residue of a cyclic or acyclic sugar alcohol is from Formula (IIa'), any suitable substituted reduced sugar alcohol may be employed, including esters of 1,4-sorbitan, esters of 2,5-sorbitan, and esters of 3,6-sorbitan. In one embodiment, the residue of at least one cyclic or acyclic sugar alcohol is selected from Formula (IIa') to be Formula (IIaa'):

In one embodiment, at least one R is a direct bond to C═O of Formula (I), or —H, and at least one R is —C(O)R¹ or R¹. Compounds used to form residues of Formula (IIaa'), having at least one R as —H and at least one R selected from —C(O)R¹, are commonly known as alkyl sorbitans. These sorbitans can be mono-substituted, di-substituted, or tri-substituted with —C(O)R¹. It is known that commercially available sorbitans, such as SPAN, contain a mixture of the various sorbitans ranging from where each R is H (unsubstituted), and sorbitans where each R is —C(O)R¹ (fully substituted); wherein R¹ is a linear or branched alkyl group having 5 to 29 carbons; and mixtures of various substitutions thereof. The commercially available sorbitans may also include amounts of sorbitol, isosorbide, or other intermediates or byproducts.

In one embodiment, at least one R is —C(O)R¹, and R¹ is a linear or branched alkyl group having 5 to 29 carbons. In another embodiment, R¹ is a linear or branched alkyl group having 7 to 21 carbons, and in a third embodiment, R¹ is a linear or branched alkyl group having 11 to 21 carbons. Preferred compounds used to form these residues include mono-, di-, and tri-substituted sorbitans derived from caprylic acid, capric acid, lauric acid, mysteric acid, palmitic acid, stearic acid, arachidic acid, behenic acid, lignoceric acid, and mixtures thereof. Particularly preferred compounds include mono-, di-, and tri-substituted sorbitan stearates or sorbitan behenins.

Optionally, R¹ is a linear or branched alkyl group having 5 to 29 carbons comprising at least 1 unsaturated bond. Examples of compounds used to form compounds of Formula (IIaa') wherein at least one R is selected from —C(O)R¹; and R¹ contains least 1 unsaturated bond, include, but are not limited to, sorbitan trioleate (i.e., wherein R¹ is —C₇H₁₄CH═CHC₈H₁₇). Other examples include but are not limited to mono-, di-, and tri-substituted sorbitans derived from palmitoleic acid, lineolic acid, arachidonic acid, and erucic acid.

In one embodiment, Formula (IIaa') is employed, wherein R is further limited to independently a direct bond to C═O of Formula (I), —H; —(CH₂CH₂O)ₙ(CH(CH₃)CH₂O)ₘR²; or —(CH₂CH₂O)ₙ(CH(CH₃)CH₂O)ₘC(O)R¹. In this embodiment, at least one R is independently —(CH₂CH₂O)ₙ(CH(CH₃)CH₂O)ₘR² or —(CH₂CH₂O)ₙ(CH(CH₃)CH₂O)ₘC(O)R¹. In one aspect, R² is H and m is a positive integer such that the substitution is hydrophobic. Compounds of Formula (IIaa'), wherein at least one R is —(CH₂CH₂O)ₙ(CH(CH₃)CH₂O)ₘR² or —(CH₂CH₂O)ₙ(CH(CH₃)CH₂O)ₘC(O)R¹, wherein each m is independently 0 to 20, each n is independently 0 to 20, and n+m is greater than 0 are known as polysorbates and are commercially available under the tradename TWEEN. These polysorbates can be mono-substituted, di-substituted, or tri-substituted with alkyl groups R¹ or R². It is known that commercially available polysorbates, contain a mixture of the various polysorbates ranging from where each R² is H (unsubstituted), and polysorbates where each R¹ is a linear or branched alkyl group having 5 to 29 carbons (fully substituted); and mixtures of various substitutions thereof. Examples of compounds of Formula (IIaa') include polysorbates such as polysorbate tristearate, and polysorbate monostearate. Examples of compounds used to form residues of Formula (IIaa') wherein m+n is greater than 0, and wherein $R^1$ comprises at least 1 unsaturated bond, include but are not limited to, polysorbate trioleate (wherein $R^1$ is $C_7H_{14}CH=CHC_8H_{17}$), are sold commercially under the name Polysorbate 80. Reagents may include mixtures of compounds having various values for R, $R^1$, and $R^2$, and may also include mixtures of compounds where $R^1$ comprises at least one unsaturated bond with compounds where $R^1$ is fully saturated.

In one embodiment, the at least one residue of a cyclic or acyclic sugar alcohol is selected from Formula (IIb'). Compounds used to form residues of Formula (IIb') are known as alkyl citrates. These citrates can be present as a mono-substituted, di-substituted, or tri-substituted compound with alkyl groups. It is known that commercially available citrates contain a mixture of the various citrates as well as citric acids from where R and each $R^4$ is —H, ranging to citrates where each $R^4$ is a linear or branched alkyl group having 6 to 30 carbons optionally comprising at least 1 unsaturated bond; and mixtures of various substitutions thereof. Mixtures of citrates having various values for $R^1$, $R^2$, and $R^4$ may be used, and may also include mixtures of compounds where $R^1$ comprises at least one unsaturated bond with compounds where $R^1$ is fully saturated. Alkyl citrates are also commercially available wherein m+n is greater than 0, $R^4$ is —$(CH_2CH_2O)_n(CH(CH_3)CH_2O)_mR^2$; or —$(CH_2CH_2O)_n(CH(CH_3)CH_2O)_mC(O)R^1$ and are present in the various substitutions from wherein R and each $R^2$ is H to wherein each $R^1$ and/or $R^2$ is a linear or branched alkyl group having 5 to 30 carbons optionally comprising at least 1 unsaturated bond. Examples of compounds used to form residues of Formula (IIb') include, but are not limited to, trialkyl citrates.

In one embodiment, the at least one residue of a cyclic or acyclic sugar alcohol is selected from Formula (IIc'). Compounds used to form residues of Formula (IIc') are known as pentaerythriol esters. These pentaerythriol esters can be present as a mono-substituted, di-substituted, or tri-substituted with alkyl groups. It is known that commercially available pentaerythriol esters contain a mixture of the various pentaerythriol esters where $R^{19}$ and each R is —H, ranging to pentaerythriol esters where each R is —$C(O)R^1$, and $R^1$ is a linear or branched alkyl group having 5 to 29 carbons optionally comprising at least 1 unsaturated bond; and mixtures of various substitutions thereof. The pentaerythriol esters also may contain compounds with mixtures of different chain lengths for R, or mixtures of compounds where $R^1$ comprises at least one unsaturated bond with compounds where $R^1$ is fully saturated.

Test Methods and Materials

Tribehenin 50, sorbitan laurate, Dipentaerythritol, SMS (sorbitan monostearate), and STS-30 (sorbitan tristearate) were obtained from DuPont Nutrition & Health, Copenhagen, Denmark.

Sorbitan trioleate was obtained from Oleon, Oleon Ertvelde, Belgium.

TWEEN 85 and TWEEN 61 were obtained from Croda, East Yorkshire, England.

Trioctyldodecyl citrate[126121-35-5] was obtained from Lubrizol, Wickliffe, Ohio.

Aerosil A200 is a fumed silica, no functionality, average particle size of 12 nm in aggregates having an average aggregate diameter of from 150-200 nm, obtained from Degussa.

MEK AC5140Z is a colloidal silica with acrylate functionality, average particle size from 70-100 nm, obtained from Nissan Chemical.

MIBK-ST is a colloidal silica, non-reactive functionality, average particle size from 10-15 nm, obtained from Nissan Chemical.

YA050C-KJA is a colloidal silica, phenyl functionality, average particle size 50 nm, obtained from Admatech.

Zinc Oxide—Degussa VP AdNano® ZnO 20 CAS 1314-13-2—fumed, 25 nm particle size.

Aluminum Oxide—Degussa Aeroxide® Alu C 805—silane coated, 13 nm particle size.

Titanium Oxide—Degussa Aeroxide® $TiO_2$ P 25—fumed, 21 nm particle size.

Test Method 1—Water Repellency

The water repellency of a treated substrate was measured according to the DuPont Technical Laboratory Method as outlined in the TEFLON Global Specifications and Quality Control Tests information packet. The test determines the resistance of a treated substrate to wetting by aqueous liquids. Drops of water-alcohol mixtures of varying surface tensions are placed on the fabric and the extent of surface wetting is determined visually. The test provides a rough index of aqueous stain resistance. The higher the water repellency rating, the better the resistance the finished substrate has to staining by water-based substances. The composition of standard test liquids is shown in the following Table 1. Ratings of 0.5 increments are determined by subtracting one half from the numbers in Table 1 for borderline passing of the test liquid.

TABLE 1

Standard Test Liquids

| Water Repellency Rating Number | Composition Vol. %, Isopropyl Alcohol | Composition, Vol. % Distilled Water |
| --- | --- | --- |
| 1 | 2 | 98 |
| 2 | 5 | 95 |
| 3 | 10 | 90 |
| 4 | 20 | 80 |
| 5 | 30 | 70 |
| 6 | 40 | 60 |
| 7 | 50 | 50 |
| 8 | 60 | 40 |
| 9 | 70 | 30 |
| 10 | 80 | 20 |
| 11 | 90 | 10 |
| 12 | 100 | 0 |

Test Method 2—Oil Repellency

The treated fabric samples were tested for oil repellency by a modification of AATCC standard Test Method No. 118, conducted as follows: A fabric sample, treated with an aqueous dispersion of polymer, was conditioned for a minimum of 15 hours at 23° C.+65% relative humidity prior to testing. A series of organic liquids, identified below in Table 2, were then applied drop wise to the fabric samples. Beginning with the lowest numbered test liquid (Repellency Rating No. 1), one drop (approximately 5 mm in diameter or 0.05 mL volume) was placed on each of three locations at least 5 mm apart. The drops were observed for 30 seconds. If, at the end of this period, two of the three drops were still spherical in shape with no wicking around the drops, three drops of the next highest numbered liquid were placed on adjacent sites and similarly observed for 30 seconds. The procedure was continued until one of the test liquids resulted in two of the three drops failing to remain spherical to hemispherical, or wetting or wicking occurred.

The oil repellency rating of the fabric was the highest numbered test liquid for which two of the three drops remained spherical to hemispherical, with no wicking for 30 seconds. Ratings of 0.5 increments were determined by subtracting one-half from the number in Table 2 for borderline passing of the next liquid. Higher ratings indicate greater repellency. The composition of oil repellency test liquids is shown in the Table 2.

TABLE 2

Oil Repellency Test Liquids

| Oil Repellency Rating | Test Solution |
|---|---|
| 1 | NUJOL Purified Mineral Oil |
| 2 | 65/35 NUJOL/n-hexadecane by volume at 21° C. |
| 3 | n-hexadecane |
| 4 | n-tetradecane |
| 5 | n-dodecane |
| 6 | n-decane |

Test Method 3—Fabric Treatment

The fabrics treated in this study were 100% by weight khaki cotton twill available from SDL Atlas Textile Testing Solutions, Rock Hill, S.C. 29732 and 100% by weight red polyester fabric available from L. Michael OY, Finland. The fabric was treated with the aqueous dispersions various emulsion polymer using a conventional pad bath (dipping) process. The prepared concentrated dispersion of the polymer emulsions were diluted with deionized water to achieve a pad bath having 60 g/L or 100 g/L of the final emulsion in the bath.

Test Method 4—Oil and Water Contact Angle Measurement

Contact angles were measured using a VCA Optima XE goniometer. Unless otherwise noted, a 1 μL drop of distilled water or hexadecane was placed on the surface and allowed to equilibrate for 10 seconds before the contact angle was measured.

For the following examples, amounts of reagents are given in percent by weight, based on the total amount of reactive agents that compose the final compound. The present invention is not to be limited by the examples.

EXAMPLES

Examples 1-10

10 samples were prepared using different isocyanate-reactive components (b) and 3-(Triethoxysilyl)propyl (component (a)), as follows:

In a small vial, component (b) and n-butyl acetate were heated to 60° C. under nitrogen. Component (a) and 0.5% $FeCl_3$ in MIBK were added and the reaction temperature was raised to 95° C. and stirred overnight. Amounts of each component are shown in Table 3. When the reaction tested negative for isocyanates, the solution, comprising the isocyanate derived organosilane, was transferred to a plastic bottle and diluted to 10% solids with n-butyl acetate.

TABLE 3

| Ex. No. | Component (b) (grams) | Component (a) (grams) | Butyl acetate (grams) | $FeCl_3$ (grams) |
|---|---|---|---|---|
| 1 | sorbitan tristearate 7.44 g | 2.50 | 9.94 | 0.17 |
| 2 | sorbitan laurate 7.9648 g | 1.006 | 8.9318 | 0.07 |
| 3 | sorbitant tribehenin 50 7.3231 g | 2.1558 | 9.4715 | 0.1469 |
| 4 | sorbitan trioleate 7.8501 g | 2.1594 | 10.047 | 0.1419 |
| 5 | Tween 85 11.6187 g | 2.1567 | 13.8191 | 0.2017 |
| 6 | Tween 61 2.6968 g | 2.1405 | 4.851 | 0.1376 |
| 7 | trioctyldodecyl citrate 6.0517 g | 2.1856 | 8.2445 | 0.1527 |
| 8 | dioctyldecyl citrate 0.9996 g | 0.508 | 2.5092 | 0.0293 |
| 9 | sorbitan monostearate 2.038 g | 2.146 | 4.1917 | 0.1671 |
| 10 | dipentaerythritol 7.9826 g | 2.1439 | 10.1754 | 0.147 |

Examples 11-20

A first sample of a fluorinated isocyanate derived reactive compound was prepared as follows. In a 500 mL reactor under nitrogen, 2-(perfluorohexyl)ethyl alcohol (100 g) and THF (tetrahydrofuran) (100 g) were heated to 60° C. under nitrogen. 3-(Triethoxysilyl)propyl isocyanate (62 g) and 0.5% $FeCl_3$ in MIBK (0.5 g) were added and the reaction temperature was raised to 85° C. and stirred overnight. When the reaction tested negative for isocyanates, the solvent was removed from the product via rotary evaporation. Thus producing a fluorinated isocyanate derived reactive compound.

Examples 11-20 were prepared by blending each sample from Examples 1-10 (shown in Table 3) with the above prepared fluorinated isocyanate derived reactive compound as follows.

In a small vial, 10 grams of each sample prepared in Examples 1-10 and 0.25 gram of the fluorinated isocyanate derived reactive compound produced above were stirred for 5 minutes before further dilution to a 1% solution with n-butyl acetate (125 g). Thus producing 10 samples of a blended compound (Examples 11-20).

Comparative Example A was prepared as follows. In a 500 mL reactor under nitrogen, 2-(perfluorohexyl)ethyl alcohol (100 g) and THF (100 g) were heated to 60° C. under nitrogen. 3-(Triethoxysilyl)propyl isocyanate (62 g) and 0.5% $FeCl_3$ in MIBK (0.5 g) were added and the reaction temperature was raised to 85° C. and stirred overnight. When the reaction tested negative for isocyanates, the solvent was removed from the product via rotary evaporation.

The obtained samples from Examples 1-20 and Comparative Example A were then applied to glass slides as follows:

Glass slides (3"×1"×1 mm) were rinsed with acetone and dried with a heat gun before placing them in a 1% solution of the samples from Examples 1-20 in n-butyl acetate in an 8 oz. HDPE jar. The reaction was catalyzed by the addition of diisopropylamine and stirred overnight. The slides were then removed and dried with a heat gun. The surface of the slides were allowed to equilibrate for at least 18 hours before water and oil contact angles were measured on the now functionalized surface.

Comparative Example B was an untreated glass substrate. Water and oil contact angles were measured on the untreated glass surface and results are reported in Table 4 as Comparative Example A.

Table 4 shows the results of the water and oil contact measurement angles for each Example.

TABLE 4

| Example # | Water Contact angle (degrees) | Standard Deviation± | Oil Contact angle (degrees) | Standard Deviation± |
|---|---|---|---|---|
| 1 | 98.967 | 1.16 | 43.65 | 3.30 |
| 2 | 87.667 | 0.67 | 11.70 | 1.41 |
| 3 | 102.1 | 0.17 | 43.45 | 0.50 |
| 4 | 66.05 | 2.23 | 10.07 | 1.71 |
| 5 | 7.9 | 0.28 | 14.95 | 0.64 |
| 6 | 62.3 | 1.22 | 28.55 | 0.78 |
| 7 | 77.667 | 0.75 | 11.70 | 0.14 |
| 8 | 101.80 | 1.61 | 39.90 | 0.61 |
| 9 | 65.1 | 0.40 | 17.30 | 1.56 |
| 10 | 105.667 | 1.17 | 45.13 | 1.89 |
| 11 | 98.46 | 2.59 | 72.63 | 2.75 |
| 12 | 85.1 | 1.55 | 22.80 | 3.68 |
| 13 | 101.6 | 0.76 | 64.20 | 0.42 |
| 14 | 69.267 | 0.50 | 14.45 | 2.62 |
| 15 | 86.375 | 3.10 | 86.00 | 9.79 |
| 16 | 69.383 | 2.54 | 39.70 | 2.39 |
| 17 | 74.62 | 2.04 | 10.63 | 0.40 |
| 18 | — | — | — | — |
| 19 | 77.7 | 1.69 | 23.13 | 2.72 |
| 20 | 102.15 | 0.72 | 73.50 | 1.56 |
| Comparative Exp. A | 122.00 | 0.28 | 77.80 | 4.82 |
| Comparative Exp. B | 18.73 | 1.41 | 11.65 | 1.43 |

Additionally, sand particles were functionalized with each sample from Examples 1-20 and Comparative Example A as follows:

In a small vial, 30-50 mesh sand (silicone dioxide, 300 μm-600 μm diameter), was stirred in a 5% solution of each sample from Examples 1-20 and Comparative Example A in n-butyl acetate. The reaction was catalyzed by the addition of diisopropylamine and stirred overnight. The functionalized sand particles were then cured in a Mathis oven set at 320° F. for 2 minutes. After allowing the surface of the sand particles to equilibrate for at least 18 hours, the particles were applied to double-sided tape on a glass slide and oil and water contact angles were measured. Results are shown in Table 5.

TABLE 5

| Example # | Water Contact angle (degrees) | Standard Deviation± | Oil Contact angle (degrees) | Standard Deviation± |
|---|---|---|---|---|
| 1 | 135.75 | 4.29 | 0.00 | 0.00 |
| 2 | 128.50 | 6.74 | 0.00 | 0.00 |
| 3 | 139.50 | 1.70 | 0.00 | 0.00 |
| 4 | 132.78 | 2.10 | 0.00 | 0.00 |
| 5 | 0.00 | 0.00 | 0.00 | 0.00 |
| 6 | 127.48 | 1.91 | 0.00 | 0.00 |
| 7 | 112.17 | 3.46 | 0.00 | 0.00 |
| 8 | 145.60 | 3.18 | 0.00 | 0.00 |
| 9 | 129.46 | 3.94 | 0.00 | 0.00 |
| 10 | 130.26 | 4.34 | 0.00 | 0.00 |
| 11 | 141.70 | 4.17 | 0.00 | 0.00 |
| 12 | 131.87 | 1.15 | 0.00 | 0.00 |
| 13 | 141.05 | 3.29 | 0.00 | 0.00 |
| 14 | 126.38 | 4.20 | 0.00 | 0.00 |
| 15 | 0.00 | 0.00 | 104.27 * 3 μL drop | 10.94 |
| 16 | 107.20 | 1.56 | 0.00 | 0.00 |
| 17 | 130.93 | 2.84 | 0.00 | 0.00 |
| 18 | 144.10 | 4.52 | 132.43 * 3 μL drop | 5.36 |
| 19 | 136.85 | 1.97 | 0.00 | 0.00 |
| 20 | 143.93 | 4.84 | 0.00 | 0.00 |
| Comparative Exp. A | 138.23 | 1.50 | 130.53 | 2.73 |

Examples 21-26

Metal oxide particles (ZnO, Al$_2$O$_3$, and TiO$_2$) were functionalized with Example 1 and Example 11 as follows. In a small vial a sample of oxide particles were stirred in a 5% solution of a sample from Example 1 in n-butyl acetate overnight with a drop of diisopropylamine. An additional sample of oxide particles were stirred in a 5% solution of a sample from Example 11 in n-butyl acetate overnight with a drop of diisopropylamine. The functionalized oxide particles were then cured in a Mathis oven set at 320° F. for 2 minutes. After allowing the surface of the oxide particles to equilibrate for at least 18 hours, the particles were applied to double-sided tape on a glass slide and oil and water contact angles were measured. Additionally, untreated oxide particles were also tested for oil and water contact angles (Comparative Examples D-F). Results are shown in Table 6.

TABLE 6

| Ex. No. | Water Contact Angle (degrees) | Standard Deviation± | Oil Contact angle (degrees) | Standard Deviation± |
|---|---|---|---|---|
| Comparative Exp. D (ZnO) | 54.48 | 5.31 | 0.00 | 0.00 |
| Example 1 (ZnO) | 145.2 * 7 μL drop | 0.141 | 0.00 | 0.00 |
| Example 11 (ZnO) | 149.6 * 7 μL drop | 1.273 | 34.633 | 6.504 |
| Comparative Exp. E (Al$_2$O$_3$) | 148.87 | 0.91 | 0.00 | 0.00 |
| Example 1 (Al$_2$O$_3$) | 145.15 * 7 μL drop | 1.344 | 0.00 | 0.00 |
| Example 11 (Al$_2$O$_3$) | 145 * 7 μL drop | 0.424 | 52.533 | 2.857 |
| Comparative Exp. F (TiO$_2$) | 62.17 | 2.04 | 0.00 | 0.00 |
| Example 1 (TiO$_2$) | 147.35 * 7 μL drop | 0.212 | 0.00 | 0.00 |
| Example 11 (TiO$_2$) | 147.4 * 7 μL drop | 0.424 | 0.00 | 0.00 |

Example 27

In a small vial, 3 g of 30-50 mesh sand (300 μm-600 μm diameter), phenyl-functionalized colloidal silica (Admatech YA050C-KJA Colloidal Silica, 50 nm diameter, 1.00 g), MIBK (4.00 g) and 10% solution of a sample from Example 1 in n-butyl acetate (0.50 g) were stirred overnight with a drop of diisopropylamine. The functionalized sand was then cured in a Mathis oven at 320° F. for 2 minutes. After allowing the surface of the sand to equilibrate for at least 18 hours, the sand was applied to double sided tape on a glass slide and water and oil contact angles were measured. Results are reported in Table 7.

Examples 28-29

In a small vial, 10% solution of a sample from Example 1 (Example 28) and a 10% solution of a sample from Example 11 (Example 29) were each combined with n-butyl acetate (5.00 g), fumed silica (Degussa Aerosil A200 Fumed silica, 150-200 nm aggregate diameter, 1.50 g), and MIBK (8.5 g) and heated to 75° C. A drop of dimethylethylamine catalyst was added and the reaction was stirred overnight. Glass slides were coated with 0.5% solutions of each and dried in a Sartorius MA35 Moisture Analyzer at 160° C. The slides were then heated with a heat gun and the surface of the slide was allowed to equilibrate for at least 18 hours before water and oil contact angles were measured. Results are reported in Table 7.

TABLE 7

| Exp. # | Water Contact Angle (degrees) | STDEV± | Oil Contact Angle (degrees) | STDEV± |
|---|---|---|---|---|
| 27 | 137.78 | 1.63 | — | — |
| 28 | 113.37 | 1.20 | 10.40 | 1.27 |
| 29 | 100.83 | 2.89 | 26.10 | 2.40 |

Examples 30-31

In a small vial, 10% solution of a sample from Example 1 (Example 30) and a 10% solution of a sample from Example 11 (Example 31) were each combined with n-butyl acetate (5.00 g) and 15% acrylate-functionalized colloidal silica (Nissan MEK-AC-5140Z, 70-100 nm) (10.00 g) and heated to 75° C. A drop of dimethylethylamine catalyst was added and the reaction was stirred overnight. Glass slides were coated with 0.5% solutions of each and dried in a Sartorius MA35 Moisture Analyzer at 160° C. The slides were then heated with a heat gun and the surface of the slide was allowed to equilibrate for at least 18 hours before water and oil contact angles were measured. Results are reported in Table 8.

TABLE 8

| Exp. # | Water Contact Angle (degrees) | STDEV± | Oil Contact Angle (degrees) | STDEV± |
|---|---|---|---|---|
| 30 | 95.00 | 0.29 | 23.07 | 6.22 |
| 31 | 90.30 | 2.78 | 36.25 | 1.77 |

Example 32

A 10% solution of acrylate-functionalized colloidal silica (Nissan MEK-AC-5140Z, 70-100 nm diameter) functionalized with 25 wt % of a sample from Example 1 in n-butyl acetate (10.00 g), D.I. water (184.30 g), stearamidopropyl dimethylamine (2.85 g), lauryl alcohol (trioxyethylene) (0.60 g), acetic acid (1.43 g), and dipropylene glycol (10.91 g) was homogenized for 8 passes at 4350 psi pressure. Solvent was removed via rotary evaporation and the dispersion was diluted to 1.5% solids with D.I. water. The silane dispersion (64.93 g) was added to a 500 mL reactor.

A solution of D.I. water (192 g), stearamidopropyl dimethylamine (4.56 g), lauryl alcohol (trioxyethylene) (0.96 g), acetic acid (2.30 g), dipropylene glycol (17.46 g), soy methyl ester (1.38 g), and stearic acid (0.01 g) was heated to 60° C. 6,2-Fluoromethacrylate (60.96 g), polyoxyethylene (7) methacrylate (0.72 g), behenyl methacrylate (21.34 g), stearyl methacrylate (3.05 g), eicosyl methacrylate (6.10 g), 2-hydroxyethyl methacrylate (2.92 g), and dodecyl mercaptan (0.6 g) were added to the heated solution and homogenized for 8 passes at 4350 psi. This dispersion was added to the 500 mL reactor containing the silane dispersion. N-methylolacrylamide 48% (1.43 g) and 2,2'-azobis(2-methylpropionamidine)dihydrochloride (0.29 g) were added and the reaction was heated to 55° C. and reacted for 8 hours. The product was then diluted to 10% solids in water and padded and cured at 320° F. for 2 minutes on cotton and polyester for testing. Testing for oil and water repellency was completed and results are reported in Table 9.

Example 33

In a small vial, 5% of a sample from Example 1 in n-butyl acetate (13.34 g) and 10-15 nm colloidal silica (Nissan MIBK-ST Colloidal Silica, 15% solids in MIBK, 6.66 g) were heated to 75° C. A drop of dimethylethylamine catalyst was added and the reaction was stirred overnight. The product was diluted to 10% solids with n-butyl acetate and 1.0 g was added to another small vial. To the same vial, MIBK (19.20 g), 6,2-fluoromethacrylate (6.10 g), polyoxyethylene (7) methacrylate (0.07 g), behenyl methacrylate (2.13 g), stearyl methacrylate (0.31 g), eicosyl methacrylate (0.61 g), 2-hydroxyethyl methacrylate (0.29 g), N-methylolacrylamide 48% (0.14 g), dodecyl mercaptan (0.06 g), and 2,2'-azobis(2-methylpropionamidine)dihydrochloride (0.03 g) were heated to 55° C. and stirred overnight. The product was diluted to 10% solids in MIBK and padded and cured at 320° F. for 2 minutes on cotton and polyester. Testing for oil and water repellency was completed and results are reported in Table 9.

Example 34

In a small vial, MIBK (19.20 g), colloidal silica (Nissan MIBK-ST Colloidal Silica, 10-15 nm diameter, 0.10 g), 6,2-fluoromethacrylate (6.10 g), polyoxyethylene (7) methacrylate (0.07 g), behenyl methacrylate (2.13 g), stearyl methacrylate (0.31 g), eicosyl methacrylate (0.61 g), 2-hydroxyethyl methacrylate (0.29 g), N-methylolacrylamide 48% (0.14 g), dodecyl mercaptan (0.06 g), and 2,2'-azobis (2-methylpropionamidine)dihydrochloride (0.03 g) were heated to 55° C. and stirred overnight. The product was diluted to 10% solids in MIBK and padded and cured at 320° F. for 2 minutes on cotton and polyester. Testing for oil and water repellency was completed and results are reported in Table 9.

Example 35

In a small vial, 10 g of a 10% solution of acrylate-functionalized colloidal silica (Nissan MEK-AC-5140Z, 70-100 nm diameter) functionalized with 25 wt. % of a sample from Example 1 in n-butyl acetate (10.00 g) and 2,2'-azobis(2-methylbutyronitrile) (0.01 g) were stirred at 70° C. overnight under nitrogen. The product was padded and cured at 320° F. for 2 minutes on cotton and polyester. Testing for oil and water repellency was completed and results are reported in Table 9.

TABLE 9

| | Cotton | | Polyester | |
|---|---|---|---|---|
| Example # | Water Drop | Oil Drop | Water Drop | Oil Drop |
| Example 32 | 6 | 5 | 6 | 5 |
| Example 33 | 7 | 5 | 7 | 5 |
| Example 34 | 7 | 5 | 7 | 5 |
| Example 35 | 3.5 | 0 | 3.5 | 0 |

What is claimed is:

1. An organosilane represented by Formula (I)

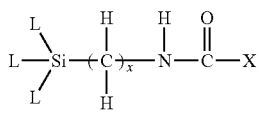

wherein:
x is an integer from 1 to 12;
L is independently chosen from H, $C_1$-$C_2$ alkyl, or OR, where R is H or $C_1$-$C_4$ alkyl; and
X is selected from Formulas (IIa'), (IIb'), or (IIc'):

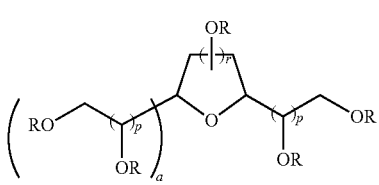

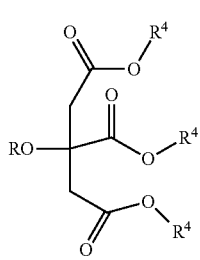

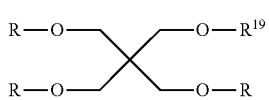

wherein each R is independently a direct bond to C=O of Formula (I), —H; —$R^1$; —C(O)$R^1$; —(CH$_2$CH$_2$O)$_n$(CH(CH$_3$)CH$_2$O)$_m$$R^2$; or —(CH$_2$CH$_2$O)$_n$(CH(CH$_3$)CH$_2$O)$_m$C(O)$R^1$;
each n is independently 0 to 20;
each m is independently 0 to 20;
m+n is greater than 0;
r is 1 to 3;
a is 0 or 1;
p is independently 0 to 2;
provided that a is 0 when r is 3;

each $R^1$ is independently a linear or branched alkyl group having 5 to 29 carbons optionally comprising at least 1 unsaturated bond;

each $R^2$ is independently H, or a linear or branched alkyl group having 6 to 30 carbons optionally comprising at least 1 unsaturated bond;

or a mixtures thereof, provided when X is Formula (IIa'), then at least one R is a —$R^1$; —C(O)$R^1$; —(CH$_2$CH$_2$O)$_n$(CH(CH$_3$)CH$_2$O)$_m$$R^2$; or —(CH$_2$CH$_2$O)$_n$(CH(CH$_3$)CH$_2$O)$_m$C(O)$R^1$;

each $R^4$ is independently a direct bond to C=O of Formula (I), —H, a linear or branched alkyl group having 6 to 30 carbons optionally comprising at least 1 unsaturated bond, or combinations thereof; —(CH$_2$CH$_2$O)$_n$(CH(CH$_3$)CH$_2$O)$_m$$R^2$;

or —(CH$_2$CH$_2$O)$_n$(CH(CH$_3$)CH$_2$O)$_m$C(O)$R^1$;

provided when X is Formula (IIb'), then at least one R or $R^4$ is a linear or branched alkyl group optionally comprising at least 1 unsaturated bond, or combinations thereof; —(CH$_2$CH$_2$O)$_n$(CH(CH$_3$)CH$_2$O)$_m$$R^2$;

or —(CH$_2$CH$_2$O)$_n$(CH(CH$_3$)CH$_2$O)$_m$C(O)$R^1$; and each $R^{19}$ is a direct bond to C=O of Formula (I), —H, —C(O)$R^1$, or —CH$_2$C[CH$_2$OR]$_3$, provided when X is Formula (IIc'), then at least one $R^{19}$ or R is —C(O)$R^1$, or —CH$_2$C[CH$_2$OR]$_3$.

2. The organosilane of claim 1 wherein the moieties X of formula (IIa'), (IIb'), and (IIc') are at least 50% bio-based derived.

3. The organosilane of claim 1 wherein the moieties X of formula (IIa'), (IIb'), and (IIc') are 100% bio-based derived.

4. The organosilane of claim 1 wherein X is selected from formula (IIa') wherein the values of R which are not directly bonded to C=O are selected from —H; —$R^1$; or —C(O)$R^1$.

5. The organosilane of claim 1 wherein X is selected from formula (IIa') wherein the values of R which are not directly bonded to C=O are selected from —H; —(CH$_2$CH$_2$O)$_n$(CH(CH$_3$)CH$_2$O)$_m$$R^2$; or —(CH$_2$CH$_2$O)$_n$(CH(CH$_3$)CH$_2$O)$_m$C(O)$R^1$.

6. The organosilane of claim 1 wherein X is selected from formula (IIb').

7. The organosilane of claim 1 wherein X is selected from formula (IIc').

8. Surface modified inorganic oxide particles comprising an oxide of M, at least one of said particles having a surface covalently bonded to at least one organosilane group represented by Formula (IV):

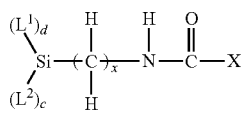

wherein:
x is an integer from 1 to 12;
$L^1$ represents an oxygen covalently bonded to an M;
each $L^2$ independently selected from the group consisting of H, a $C_1$-$C_2$ alkyl, and OH; d and c are integers such that: d≥1, c≥0, d+c=3;

X is selected from Formulas (IIa'), (IIb'), or (IIc'):

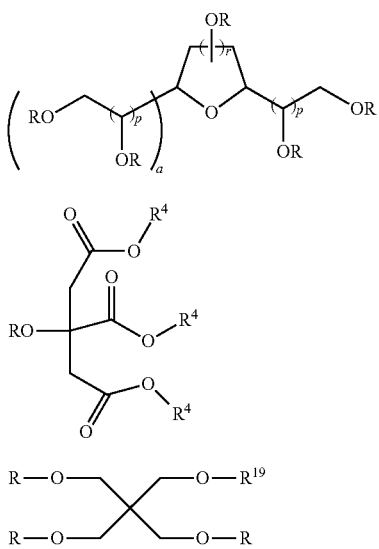

(IIa')

(IIb')

(IIc')

wherein each R is independently a direct bond to C=O of Formula (I), —H; —R$^1$; —C(O)R$^1$; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$;

each n is independently 0 to 20;
each m is independently 0 to 20;
m+n is greater than 0;
r is 1 to 3;
a is 0 or 1;
p is independently 0 to 2;
provided that a is 0 when r is 3;
each R$^1$ is independently a linear or branched alkyl group having 5 to 29 carbons optionally comprising at least 1 unsaturated bond;
each R$^2$ is independently —H, or a linear or branched alkyl group having 6 to 30 carbons optionally comprising at least 1 unsaturated bond;
or a mixtures thereof,
provided when X is Formula (IIa'), then at least one R is a —R$^1$; —C(O)R$^1$; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$;
each R$^4$ is independently a direct bond to C=O of Formula (I), —H, a linear or branched alkyl group having 6 to 30 carbons optionally comprising at least 1 unsaturated bond, or combinations thereof; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$;
provided when X is Formula (IIb'), then at least one R or R$^4$ is a linear or branched alkyl group optionally comprising at least 1 unsaturated bond, or combinations thereof; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$; and
each R$^{19}$ is a direct bond to C=O of Formula (I), —H, —C(O)R$^1$, or —CH$_2$C[CH$_2$OR]$_3$,
provided when X is Formula (IIc'), then at least one R$^{19}$ or R is —C(O)R$^1$, or —CH$_2$C[CH$_2$OR]$_3$.

9. The surface modified inorganic oxide particles of claim 8, wherein M is Ti.

10. The organosilane of claim 1 wherein formula (IIa) is further defined as formula (IIaa'):

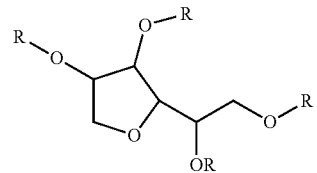

(IIaa')

wherein R is independently a direct bond to C=O of Formula (I), —H; —(CH$_2$CH$_2$O)$_n$(CH(CH$_3$)CH$_2$O)$_m$R$^2$; or —(CH$_2$CH$_2$O)$_n$(CH(CH$_3$)CH$_2$O)$_m$C(O)R$^1$.

11. The organosilane of claim 1 wherein formula (IIa) is further defined as formula (IIaa')

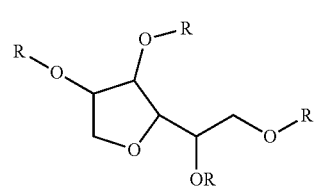

(IIaa')

wherein R is independently C(O)R$^1$, H, or a direct bond to C=O of Formula (I).

12. The surface modified inorganic oxide particles of claim 8, further comprising an at least partial surface coating.

13. The organosilane of claim 1, wherein the organosilane is blended with at least one fluorosilane.

14. The organosilane of claim 1, wherein L is CH$_3$.

15. An organosilane represented by Formula (I)

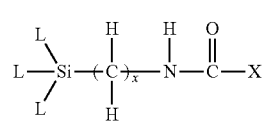

(I)

wherein:
x is an integer from 1 to 12;
L is independently chosen from a H, C$_1$-C$_2$ alkyl, or OR, where R is H or C$_1$-C$_4$ alkyl; and
X is at least one residue of an ester of a cyclic or acyclic sugar alcohol which is substituted with at least one —C(O)R$^1$, —(CH$_2$CH$_2$O)$_n$(CH(CH$_3$)CH$_2$O)$_m$C(O)R$^1$, or mixtures thereof;
where the cyclic or acyclic sugar alcohol is selected from glucose, glyceraldehyde, erythrose, arabinose, ribose, arabinose, allose, altrose, mannose, xylose, lyxose, gulose, glactose, talose, fructose, ribulose, mannoheptulose, sedoheltpulose, threose, erythritol, threitol, glucopyranose, mannopyranose, talopyranose, allopyranose, altropyranose, idopyranose, gulopyranose, glucitol, mannitol, erythritol, sorbitol, arabitol, xylitol, ribitol, galactitol, fucitol, iditol, inositol, pentaerythritol, dipentaerythritol, volemitol, gluconic acid, glyceric acid, xylonic acid, galactaric acid, ascorbic acid, citric acid, gluconic acid lactone, glyceric acid lactone, xylonic acid lactone, glucosamine, galactosamine, or mixtures thereof;
wherein each n is independently 0 to 20; each m is independently 0 to 20; m+n is greater than 0; and each $R^1$ is independently a linear or branched alkyl group having 5 to 29 carbons optionally comprising at least 1 unsaturated bond.

16. Surface modified inorganic oxide particles comprising an oxide of M, at least one of said particles having a surface covalently bonded to at least one organosilane group represented by Formula (IV):

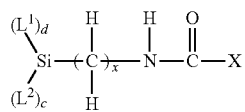

(IV)

wherein:
x is an integer from 1 to 12;
$L^1$ represents an oxygen covalently bonded to an M;
X is at least one residue of an ester of a cyclic or acyclic sugar alcohol which is substituted with at least one $-C(O)R^1$, $-(CH_2CH_2O)_n(CH(CH_3)CH_2O)_mC(O)R^1$, or mixtures thereof;

where the cyclic or acyclic sugar alcohol is selected from glucose, glyceraldehyde, erythrose, arabinose, ribose, arabinose, allose, altrose, mannose, xylose, lyxose, gulose, glactose, talose, fructose, ribulose, mannoheptulose, sedoheltpulose, threose, erythritol, threitol, glucopyranose, mannopyranose, talopyranose, allopyranose, altropyranose, idopyranose, gulopyranose, glucitol, mannitol, erythritol, sorbitol, arabitol, xylitol, ribitol, galactitol, fucitol, iditol, inositol, pentaerythritol, dipentaerythritol, volemitol, gluconic acid, glyceric acid, xylonic acid, galactaric acid, ascorbic acid, citric acid, gluconic acid lactone, glyceric acid lactone, xylonic acid lactone, glucosamine, galactosamine, or mixtures thereof;

wherein each n is independently 0 to 20; each m is independently 0 to 20; m+n is greater than 0; each $R^1$ is independently a linear or branched alkyl group having 5 to 29 carbons optionally comprising at least 1 unsaturated bond; and each $L^2$ independently selected from the group consisting of H, a $C_1$-$C_2$ alkyl, and OH; d and c are integers such that: d≥1, c≥0, d+c=3.

* * * * *